United States Patent
Hayashi (10) Patent No.: US 6,804,549 B2
(45) Date of Patent: Oct. 12, 2004

(54) SENTINEL LYMPH NODE DETECTION METHOD AND SYSTEM THEREFOR

(75) Inventor: Katsumi Hayashi, Kaisei-machi (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 514 days.

(21) Appl. No.: 09/841,729

(22) Filed: Apr. 25, 2001

(65) Prior Publication Data

US 2002/0013531 A1 Jan. 31, 2002

(30) Foreign Application Priority Data

Apr. 25, 2000 (JP) ........................................ 2000-124600

(51) Int. Cl.$^7$ .............................. A61B 6/00; G01T 1/161
(52) U.S. Cl. ....................................... 600/431; 250/302
(58) Field of Search ................................ 600/431, 407, 600/12, 3; 250/302, 259, 459.1, 483.1; 424/1.11, 4, 9.1, 9.3, 9.4

(56) References Cited

U.S. PATENT DOCUMENTS

| | | | | |
|---|---|---|---|---|
| 6,002,480 A | * | 12/1999 | Izatt et al. ................... | 356/479 |
| 6,167,297 A | * | 12/2000 | Benaron ...................... | 600/431 |
| 6,350,431 B1 | * | 2/2002 | Snow et al. .................. | 424/9.6 |
| 6,512,943 B1 | * | 1/2003 | Kelcz .......................... | 600/436 |
| 6,636,755 B2 | * | 10/2003 | Toida .......................... | 600/407 |
| 6,650,928 B1 | * | 11/2003 | Gailly et al. ................. | 600/425 |
| 6,662,040 B1 | * | 12/2003 | Henrichs et al. ............. | 600/431 |
| 6,671,540 B1 | * | 12/2003 | Hochman .................... | 600/431 |

FOREIGN PATENT DOCUMENTS

| | | | |
|---|---|---|---|
| WO | WO 98/48838 A1 | 11/1998 | |
| WO | WO 98/48845 | 11/1998 | .......... A61K/49/00 |
| WO | WO 00/45855 A2 | 8/2000 | |

OTHER PUBLICATIONS

Elsevier Science Publishers, Amsterdam, NL; Noguchi M. et al; "A Multicenter validation study of sentinel lymph node biopsy by the Japanese Breast Cancer Society"; Database accession No. 2000375102 XP002226130.

US National Library of Medicine (NLM), Bethesda, MD; Motomura K. et al; "Sentinel node biopsy guided by indocyanine green dye in breast cancer patients"; Database accession No. NLM10721942 XP002226131.

Elsevier Scinece Publishers, Amsterdam, NL; Nimura H. et al.; "Sentinel node navigation by ICG using infrared ray electronic endoscopy "; retrieved from STN Database accession No. 2001227609 XP002226132.

Hawrysz D. J. et al; "Developments toward diagnostic breast cancer imaging using near–infrared optical measurements and fluorescent contract agents" Database accession No. NLM11191107 XP002226133; vol. 2; no. 5 Sep. 2000; pp. 388–417.

* cited by examiner

Primary Examiner—Daniel Robinson
(74) Attorney, Agent, or Firm—Sughrue Mion, PLLC

(57) ABSTRACT

A method and system by which the sentinel lymph node, which is the first lymph node to which cancer is transferred when cancer is transferred to lymph nodes, is detected easily and with a high degree of accuracy. A fluorescent colorant is injected near a tumor, and after a predetermined period of time an abdominal operation is performed and stimulating light is projected onto the area being examined. Because the fluorescent colorant has been accumulated on the sentinel lymph node, it emits fluorescent light, which is then magnified and converted to a visual image. The examiner can view the normal image and the visible image at the same time. Because the stimulating light is in the near-infrared wavelength band, which is difficult for the fatty and other tissue that cover the sentinel lymph node to absorb, the sentinel lymph node is detected from the surface of the tissue.

35 Claims, 8 Drawing Sheets

SENTINEL LYMPH NODE DETECTION METHOD AND SYSTEM THEREFOR

BACKGROUND OF THE INVENTION

1. Field of the Invention

The present invention relates to a method of detecting sentinel lymph nodes, into which tumor cells first enter from the primary nidus of a tumor, and a system therefor.

2. Description of the Related Art

In recent years, the rate of early detection of cancer has been on the rise, and early surgical removal of cancerous growths is frequently performed. Generally, the objective of early surgical removal of cancerous growths is the complete arresting of the disease, and frequently, in addition to the diseased tissue, a plurality of lymph nodes in the area surrounding the diseased tissue, from which there is a suspected danger of transferal of the disease, are also removed. In addition, after removal of the lymph nodes an examination to determine the cause of the disease and whether or not the disease has been transferred thereto is conducted thereon, and the course of post-surgical treatment is determined.

Due to the fact that it is not known whether or not the disease has been transferred to the lymph nodes during performance the surgical removal thereof, a plurality of lymph nodes in the surrounding vicinity of the diseased tissue is removed, and the burden on the patient is therefore great. Further, in the early stages of breast cancer, for example, the rate of transfer of the disease to lymph nodes is 20 percent, for the 80 percent of the patients in whom the disease has not been transferred to the lymph nodes, the removal thereof is unnecessary.

In recent years, there has been a movement to obtain both the complete arresting of cancer attained through surgical removal of the cancerous tissue while preserving the QOL (Quality of Life) of the patient. To this end, one surgical method that has received much attention, which is aimed at preventing unnecessary removal of lymph nodes, is sentinel node navigation surgery. Hereinafter, a simple explanation of sentinel node navigation surgery will be given.

For cases in which cancer has been transferred to lymph nodes, it has recently become clear, in light of recent research, that it is not transferred randomly, but is transferred through the lymph system to the lymph nodes according to a set pattern. The first lymph node into which cancer cells enter from the primary nidus of a cancer is called a sentinel lymph node. It is believed that for cases in which cancer has been transferred to the lymph nodes, the cancer has definitely been transferred to a sentinel lymph node.

Accordingly, by finding and excising the sentinel lymph node in a cancer removal surgery performed in the early stages of the disease and performing a biopsy on the excised sentinel lymph node, and expediently diagnosing the cause of the disease, it can be determined whether or not the cancer has been transferred to the lymph nodes.

For cases in which the cancer is found to not have been transferred to the lymph nodes, it is unnecessary to remove the remaining lymph nodes. For cases in which the cancer is found to have been transferred to the lymph nodes, depending upon the conditions, a plurality of lymph nodes are surgically removed from the vicinity surrounding the diseased tissue.

By performing sentinel node navigation surgery, it becomes unnecessary to remove lymph nodes of patients for whom it has been determined that cancer has not been transferred to their lymph nodes, and the burden on such patients is reduced. Moreover, this type of surgery is not limited to breast cancer, but can be employed in conjunction with open gastrointestinal tract surgery or procedures utilizing a laparoscope.

There is a strong demand for a method of accurately and easily detecting the sentinel lymph node when performing sentinel node navigation surgery. One conventional method of detecting the lymph node is the colorant method, employing a blue colorant. According to this method, a blue colorant is locally injected, endermically or by use of an endoscope, into the vicinity surrounding the diseased area directly preceding the performance of cancer removal surgery. The injected blue colorant advances from the position at which it was injected toward the lymph nodes, and reaches the sentinel lymph node 5–15 minutes after injection.

The examiner visually detects the sentinel lymph node, which has been dyed blue. However, lymph nodes are often covered with fatty tissue, etc., and the sentinel lymph node must be searched for while such tissue is peeled away, which makes for a time consuming detection process. Moreover, while such searching and peeling away of tissues obstructing view of the sentinel lymph node is being performed, there are incidences in which the blue colorant advances beyond the sentinel lymph node and reaches other lymph nodes, whereby a problem arises in that it becomes difficult to detect the sentinel lymph node.

In addition, a method employing radioisotopes an, RI method, has also been developed. According to the Ri method, a radioisotope is locally injected, endermically or by use of an endoscope, on the day prior to surgery into the vicinity surrounding the diseased area. The injected radioisotope advances from the position at which it was injected towards the lymph nodes and stays for a set duration at the sentinel lymph node. A few hours after the radioisotope is injected a lymphosynthography is performed, and the approximate position is marked. When the surgery to remove the cancer is performed, the marked position is cut open, and employing a cancer gamma-probe, the gamma radiation emitted by the lymph nodes in the vicinity of the opened position is detected; the lymph node emitting the most gamma radiation is detected as the sentinel lymph node. According to the RI method, because the tracer reaches the lymph nodes beyond the sentinel lymph node in a short time and detection of the sentinel lymph node does not become difficult, and the sentinel lymph node can be detected even though it is covered with fatty, etc. tissue, although the detection rate is improved, because radiation is employed, management of the surgical procedure is complicated, and because a gamma probe is used, problems arise in that the detection process must be performed point-by-point and the information obtained cannot be made into an image, and the procedure is expensive.

On the other hand, in recent years a method employing fluorescent colorants, the fluorescent colorant method, for detecting diseased tissue has been proposed; a method as disclosed in PCT International Publication No. WO98/48845 for example, wherein a cyanine colorant is thrown onto a living tissue, and by irradiation thereof by stimulating light, the diseased tissue is detected.

According to the fluorescent colorant method disclosed in aforementioned WO98/48845, a photosensitive material that emits fluorescent light upon stimulation thereof by a stimulating light is applied in advance as a fluorescent diagnostic agent to the tissue that is the subject of an examination. Stimulating light in the wavelength band to which the fluorescent diagnostic agent is sensitive is irradiated onto the diseased tissue, causing fluorescent light to be emitted from the fluorescent diagnostic agent accumulated thereon, and the area into which the fluorescent diagnostic agent has permeated, which contains the diseased tissue, is detected by reception of this fluorescent light. In addition, it is indicated that the fluorescent diagnostic agent is also accumulated on the sentinel lymph node, and that detection thereof is possible.

However, in aforementioned PCT International Publication No. WO98/48845, there is no mention of a definite sentinel lymph node detection method or system. Further, regardless of the fact that the fluorescent colorant method disclosed therein suffers the same difficulty in detecting the sentinel lymph node due to the covering thereof by fatty, etc. tissues, as in the normal detection method, there is a problem in that no consideration is addressed therein to this difficulty.

SUMMARY OF THE INVENTION

The present invention has been developed in consideration of the circumstances described above, and it is a primary objective of the present invention to provide a sentinel lymph node detection method and system therefor capable of accurately and easily detecting the sentinel lymph node by use of a fluorescent colorant.

According to the first sentinel lymph node detection system of the present invention, the fluorescent light, which is close to the near-infrared wavelength band, emitted from the near-infrared fluorescent colorant that has been injected into the area of tissue under examination in the vicinity of the diseased portion, which contains the sentinel lymph node, upon irradiation thereof by stimulating light, is focused as a near-infrared fluorescent image, and the near-infrared fluorescent image is converted to a visible image.

In addition, a method can also be adopted wherein a normal image composed of the reflected light reflected by the area of tissue under examination that has been irradiated by an illuminating light, which is composed of visible light, can be superposed with the visible image that has been converted from the near-fluorescent image, and observed.

Further, a method wherein the normal image can be superposed with aforementioned visible image and focused, and the focused image observed, as a visible image, is also preferable.

According to the second sentinel lymph node detection system of the present invention, the fluorescent light, which is close to the near-infrared wavelength band, emitted from near-infrared fluorescent colorant that has been injected into the area of tissue under examination in the vicinity of the diseased portion, which includes the sentinel lymph node, upon irradiation thereof by stimulating light, is photographed by a fluorescent image photographing means, and based on the photographed near-infrared fluorescent image, a visible image is formed, and the visible image displayed.

In addition, a method can also be adopted wherein a normal image of the reflected light reflected by the area of tissue under examination that has been irradiated by an illuminating light is photographed as a normal image, said normal image is made into a normal image and superposed with the visible image, and the superposed image displayed.

It is preferable that the normal image be photographed as a color mage.

In addition, the first sentinel lymph node detection system according to the present invention comprises a stimulating light projecting means for projecting stimulating light, which has a wavelength in the wavelength range of light that stimulates the near-infrared fluorescent colorant, onto the area of tissue under examination in the vicinity of the diseased portion, which includes the sentinel lymph node and into which said near-infrared fluorescent colorant for emitting fluorescent light having a wavelength band within the near-infrared wavelength band has been injected in advance, a fluorescent light image focusing means for focusing the fluorescent light having a wavelength band within the near-infrared wavelength band emitted from the near-infrared fluorescent colorant injected into the area of tissue under examination, and a visible-image converting means for converting the fluorescent image having a wavelength band within the near-infrared wavelength band focused by the fluorescent light image focusing means to a visible image composed of light having a wavelength band within the visible spectrum.

Here, "the near-infrared wavelength band" refers to the 700 nm to 1500 nm band of frequencies.

In addition, "converting means" refers to a means for converting a near-infrared fluorescent image to a visible image; for example, an IR converter, IR viewer, etc. that converts near-infrared light input thereto to visible light and outputs said visible light.

Further, the first sentinel lymph node detection system according to the present invention may also be provided with an illuminating-light projecting means for projecting illuminating light composed of visible light onto the area of tissue under examination, and an observation means for observing the normal image composed of the illuminating light reflected by the area of tissue under examination image superposed with the visible image, which has been converted from the near-infrared image.

Still further, it is preferable that the first sentinel lymph node detection system according to the present invention also have a focusing means for superposing said normal image with said visible image, and focusing the superposed image, and an observation means for observing the image focused by the focusing means and the visible image.

The second sentinel lymph node detection system according to the present invention comprises a stimulating light projecting means for projecting stimulating light, which has a wavelength in the wavelength range of light that stimulates the near-infrared fluorescent colorant, onto the area of tissue under examination in the vicinity of the diseased portion, which includes the sentinel lymph node and into which said near-infrared fluorescent colorant for emitting fluorescent light having a wavelength band within the near-infrared wavelength band has been injected in advance, a fluorescent image photographing means for photographing the fluorescent light having a wavelength band within the near-infrared wavelength band emitted from the near-infrared fluorescent colorant injected into the area of tissue under examination, a fluorescent image forming means for forming a visible image based on the fluorescent image having a wavelength band within the near-infrared wavelength band photographed by said fluorescent image photographing means, and a display means for displaying said visible image.

In addition, the second sentinel lymph node detection system according to the present invention comprises an illuminating light projecting means for projecting illuminating light composed of visible light onto the area of tissue under examination, a normal image photographing means for photographing the normal image composed of the reflected light reflected by the area of tissue under examination upon illumination thereof by the illuminating light, a normal-image forming means for forming a normal image from the photographed signal photographed by the normal image photographing means, and a superposed image forming means for forming a superposed image of the superposed visible image and normal image, wherein the display means can be a means for displaying superposed images.

It is preferable that a color image photographing means be utilized as aforementioned normal image photographing means. It is preferable that the fluorescent light image focusing means, the converting means and the observation means, or the fluorescent image photographing means, the fluorescent image forming means, the normal image photographing means, the normal-image forming means, the superposed image forming means and the display means are constructed in the form of a pair of goggles, a laparoscope, or a microscope.

It is preferable that the wavelength band of aforementioned stimulating light be a wavelength and of 700 nm or larger.

In this case, in order to improve the stimulating light absorption rate of the near-infrared fluorescent colorant, it is desirable that light having a wavelength band near the peak frequency of the spectra of light that can be absorbed by the near-infrared fluorescent colorant be utilized as the stimulating light.

Further, when the near-infrared fluorescent colorant is irradiated by stimulating light, it is preferable that the largest wavelength of light absorbed by the near-infrared fluorescent colorant be 700 nm or larger.

It is optimal that a cyanine colorant, of which the largest absorbable wavelength is within the near-infrared wavelength band, be utilized as the near-infrared fluorescent colorant; in particular, it is preferable that indocyanine green be utilized.

Normally, there are many occurrences in which sentinel lymph nodes are covered in fatty, etc. tissues, when sentinel lymph node detection employing the fluorescent colorant method is performed, due to the fatty, etc. a great deal of stimulating light and fluorescent light are absorbed by the tissue covering the sentinel lymph node, and there is a fear that accuracy in detecting the sentinel lymph node becomes reduced, or that detection of the sentinel lymph node becomes impossible.

Figure 1:
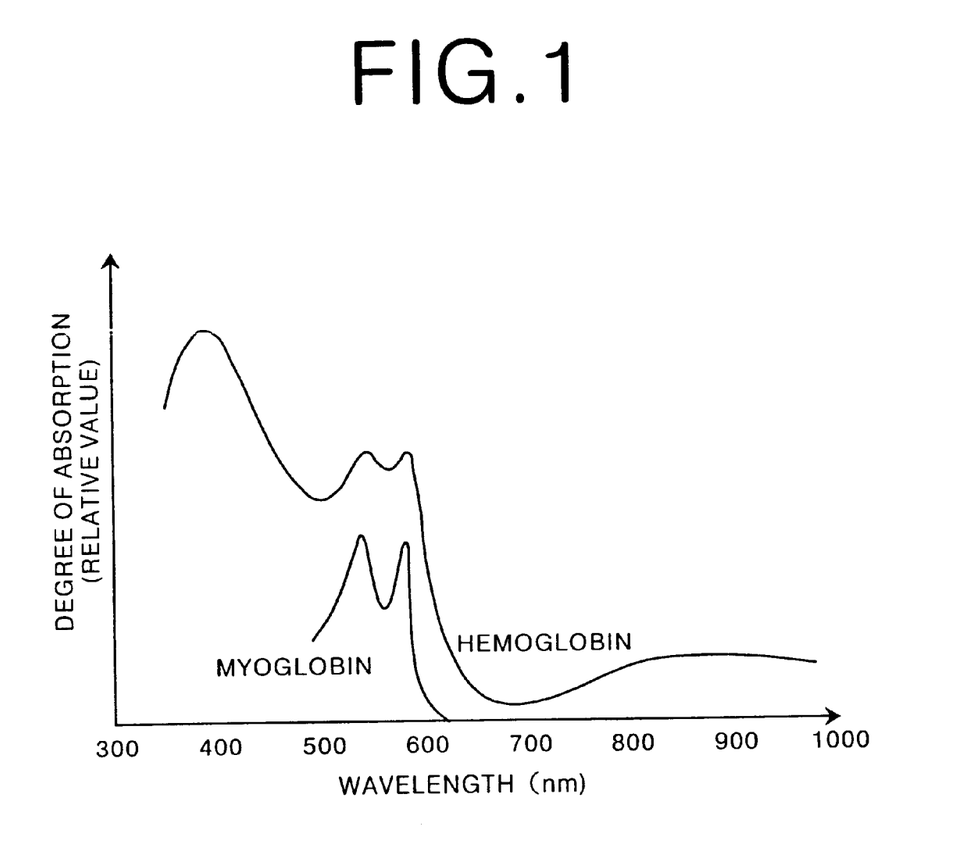
FIG. 1 is a graph provided for explaining the degree of absorption for hemoglobin, etc.

FIG. 1 shows the degree of absorption for hemoglobin, etc. contained in living tissue; it is known that wavelengths of light in the visible spectra are easily absorbed by living tissue, and that wavelengths above approximately 700 nm are difficult for living tissue to absorb. Because of this, if the wavelengths of both the stimulating and the fluorescent light are near the near-infrared wavelength band (700 nm–1500 nm), it is difficult for the stimulating light and the fluorescent light to be affected by the fatty, etc. tissue covering a sentinel lymph node.

In addition, because autofluorescence does not occur in living tissue due to exposure thereof to near-infrared wavelengths of light, this can contribute to improving the S/N ratio during observation.

According to the first sentinel lymph node detection system described above, a near-infrared fluorescent colorant is locally injected in advance into the vicinity of diseased tissue, and light having a wavelength band in the near-infrared range is projected as stimulating light onto the area within the part of the vicinity into which the near-infrared fluorescent colorant has been injected where the sentinel lymph node is presumed to be. Because the stimulating light is in the near-infrared wavelength band, even if the sentinel lymph node is covered by fatty, etc. tissue, it is easy for the stimulating light to reach the sentinel lymph node. In addition, because the near-infrared fluorescent colorant for emitting near-infrared fluorescent light has been accumulated on the sentinel lymph node in advance, because it is also easy for the fluorescent light emitted from the sentinel lymph node to reach the surface of the tissue, by converting the near-infrared fluorescent image emitted from the area of the tissue under examination into a visible image and displaying said visible image, the sentinel lymph node can be detected easily and with a high degree of accuracy.

In addition, by providing an observation means for superposing a normal image, which is formed of light reflected by the area of tissue under examination upon illumination thereof by illuminating light in the visible spectra, with a visible image, and observing this superposed image and the visible image, the examiner can observe both said visible and said normal image at the same time, and can easily confirm the position of the sentinel lymph node contained within the area of the tissue under examination.

Further, if aforementioned observation means is also provided with an image focusing means for superposing the normal image with the visible image and focusing the superposed image, and an observation optical means for observing this superposed image and the visible image, because the positions of the normal image and the visible image are substantially matched, the visual verifiability when the normal image and the visible image are observed at the same time is improved.

According to the first sentinel lymph node detection system: a near-infrared fluorescent colorant is locally injected in advance into the vicinity of diseased tissue; light having a wavelength band in the near-infrared wavelength range is projected as stimulating light onto the area within the part of the vicinity into which the near-infrared fluorescent colorant has been injected where the sentinel lymph node is presumed to be; the near-infrared fluorescent light emitted from the area of the tissue under examination is photographed by a fluorescent image photographing means, and by displaying said photographed image as a visible image, even for cases in which the sentinel image is covered by fatty, etc. tissue, it is easy for the stimulating light to reach the sentinel lymph node, and because it is also easy for the fluorescent light emitted from the near-infrared fluorescent colorant accumulated on the sentinel lymph node to reach the surface of the tissue, the sentinel lymph node is easily displayed as a visual image, and thereby, the sentinel image can be easily detected with a high degree of accuracy.

In addition, because the fluorescent light emitted from the sentinel lymph node can be rendered as a visible image, it is possible to halt or record a displayed image, and the ease with which the sentinel lymph node is detected is improved one level.

Further, by displaying a superposed image formed of the normal image composed of reflected illuminating light superposed with the fluorescent image, the examiner can observe the fluorescent image and the normal image at the same time, and the position of the sentinel lymph node contained within the area of tissue under examination can be easily confirmed.

If the normal image is photographed as a color image, the relative relation of the actual position of the area of tissue under examination to that of the displayed position thereof can be confirmed, and identification of the sentinel lymph node becomes easy.

If the sentinel lymph node detection system described above is constructed in the form of a pair of goggles, when performing detection of the sentinel lymph node, the examiner can freely use both hands, and ease of operability of the system is thereby improved.

Further, if the sentinel lymph detecting system is constructed in the form of a laparoscope, when performing detection of the sentinel lymph node, there is no need to carryout an abdominal operation and the burden on the patient is thereby reduced.

Still further, if the sentinel lymph node detection system described above is constructed in the form of a microscope, when performing detection of the sentinel lymph node, the detailed position of the sentinel lymph node can be confirmed, whereby the fear of inflicting damage to the surrounding tissues of the sentinel lymph node during performance of the surgical procedure to remove the sentinel lymph node is reduced, and the burden on the patient is reduced.

If the wavelength of the stimulating light is 700 nm or larger, it is difficult for it to be absorbed by the tissue. In addition, if the largest wavelength absorbable by the near-infrared fluorescent colorant is 700 nm or larger, the stimulating light is efficiently absorbed by the near-infrared fluorescent colorant.

As described above, if a cyanine colorant, of which the largest absorbable wavelength is near the near-infrared wavelength band, is utilized as the near-infrared fluorescent colorant, when said near-infrared fluorescent colorant is irradiated by stimulating light having a wavelength band in the near-infrared range, fluorescent light is efficiently emitted therefrom. In particular, if Indocyanine green is utilized, not only is absorption by the tissue not affected by dispersion, but because there is no adverse effect due to background autofluorescence, when focusing and photographing the fluorescent light emitted by the sentinel lymph node, only the fluorescent light that is the object of said focusing and photographing can be easily focused and photographed, and the reliability of the system can be improved.

DESCRIPTION OF THE PREFERRED EMBODIMENTS

Figure 2:
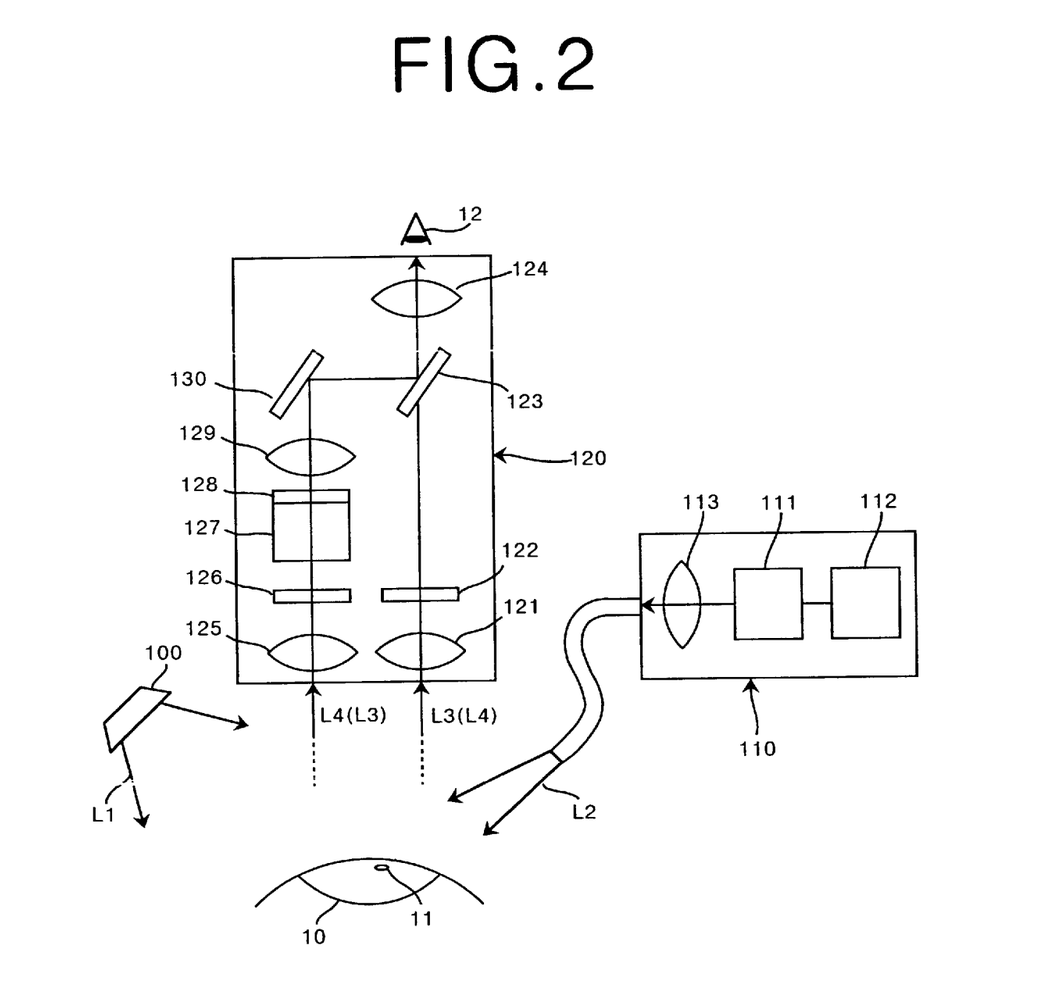
FIG. 2 is a schematic drawing of a sentinel lymph node detection system according to the present invention.

Hereinafter the preferred embodiments of the present invention will be explained with reference to the drawings. FIG. 2 is a schematic view of the configuration of a sentinel lymph node detection system according to the first embodiment of the present invention; according to this system, the near-infrared fluorescent colorant indocyanine green is locally injected in advance into the vicinity of a tumor, and the fluorescent light emitted from the area of tissue under examination, upon irradiation thereof by stimulating light, is observed by use of a goggle type observation unit and detection of the sentinel lymph node is performed.

The sentinel lymph node detection system of the current embodiment comprises a fluorescent lamp 100, a stimulating light projecting unit 110, which is provided with a light source for producing fluorescent-image observation use near-infrared stimulating light, and a goggle type observation unit 120 to be worn by an examiner for performing observation. Note that a typical configuration of the eyepiece of one side of the observation unit 120 is shown in FIG. 2; actually, the observation unit is provided as a goggle type unit providing for viewing by both eyes.

Fluorescent lamp 100 is a fluorescent lamp for emitting white light L1 as illuminating light composed of visible light, which, by electricity supplied from an off-the-shelf general electrical power source, flashes at a frequency cycle of 50 Hz.

Stimulating light projecting unit 110 is provided with a semiconductor laser 111 for producing stimulating light L2 having a wavelength of 790 nm, and a stimulating light source-use driver 112, which is electrically connected to semiconductor laser 111. Stimulating light source-use driver 112 is connected to an off-the-shelf general electrical power source (not shown), and in addition, controls the emission timing of semiconductor laser 111 so that the stimulating light L2 is emitted from semiconductor laser 111 in the cycle which is the reverse of that of fluorescent light 110.

Observation unit 120 comprises an objective lens, a near-infrared cutoff filter 122, a half mirror 123, an eyepiece 124, an objective lens 125, a near-infrared cutoff filter 126, an image intensifier 127, a fluorescent light panel 128, a lens 129, and a mirror 130.

Near-infrared cutoff filter 122 cuts off light having a wavelength of 700 nm or larger, and near-infrared cutoff filter 126 cuts off light having a wavelength of 820 nm or smaller.

Note that objective lens 125 and near-infrared cutoff filter 126 compose the fluorescent light image focusing means of the invention; fluorescent light panel 128 composes the converting means, and mirror 130, half mirror 123, objective lens 121, lens 129, and objective lens 124 compose the observation means. In particular, objective lens 121 composes the image focusing means of the invention, and eyepiece 124 composes the observation optical means.

Hereinafter, the operation of the sentinel lymph node detection system according to the first embodiment will be explained.

An example of detecting a sentinel lymph node in a case in which the patient has a tumor in his or her gastrointestinal tract will be used for the purpose of explanation.

Figure 3:
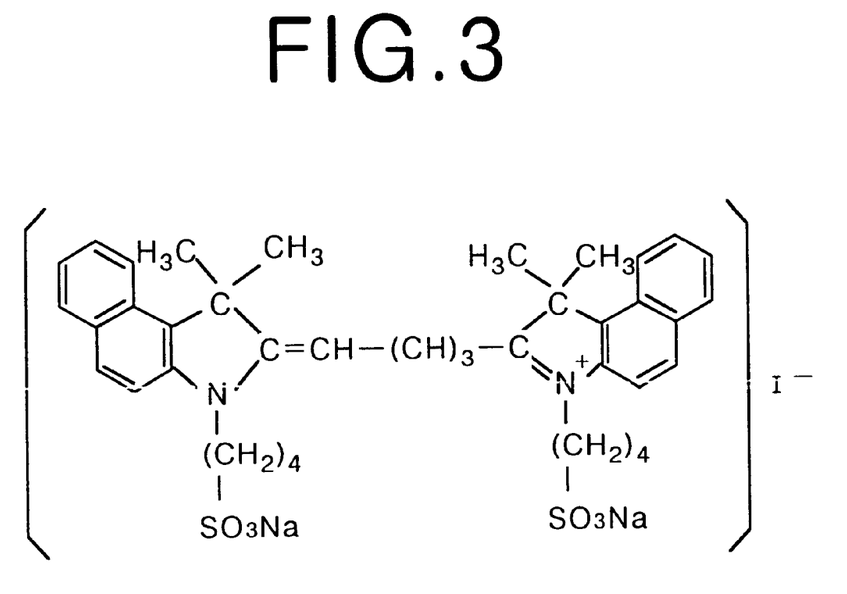
FIG. 3 shows the chemical formula of Indocyanine green.
Figure 4:
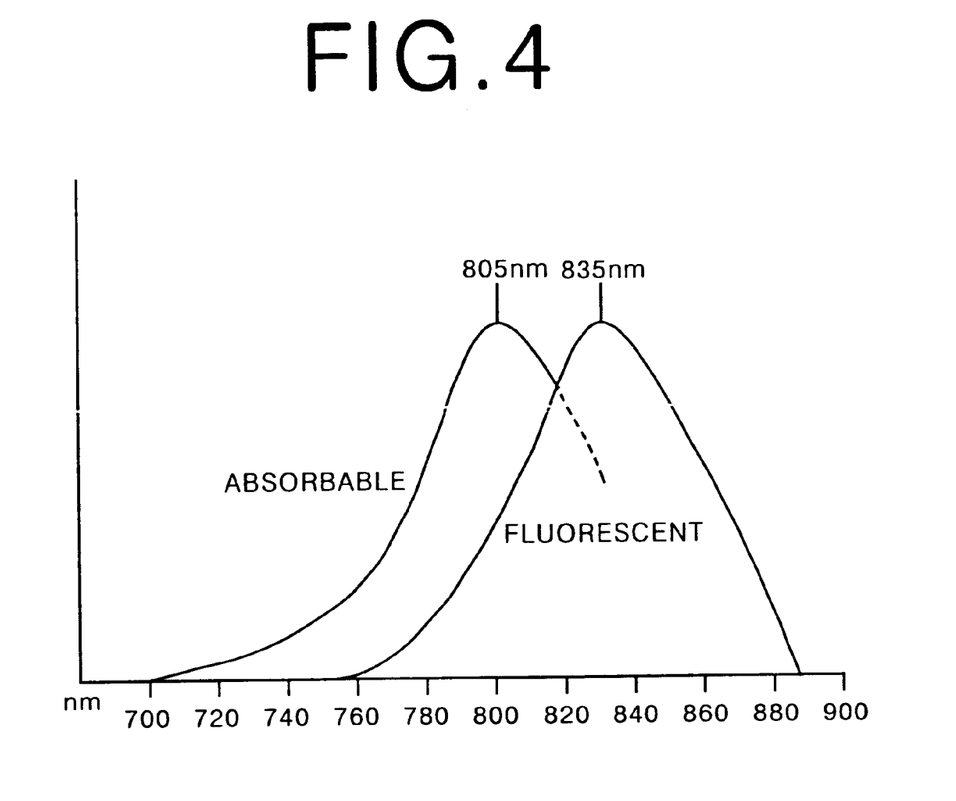
FIG. 4 shows the absorption spectrum of indocyanine green and the fluorescent spectrum.

First, at a predetermined time prior to the performance of an abdominal operation, an endoscope is inserted into the patient's gastrointestinal tract, and 5 mg of indocyanine green per each 1 Kg of body weight of the patient is locally injected into the vicinity of the tumor via an opening in a forceps. Indocyanine green is a cyanine colorant, and the chemical formula thereof is shown in FIG. 3. In addition, indocyanine green that has been bound to blood plasma protein displays an absorption spectrum and a fluorescent spectrum as shown in FIG. 4; the largest absorbable wavelength is 805 nm and the largest fluorescent light wavelength is 835 nm.

After passage of a predetermined period of time, when performing open abdominal surgery, the indocyanine green injected into the vicinity of the tumor passes through the lymph system and is accumulated on a sentinel lymph node 11. The sentinel lymph node 11 is covered by a less than 1 cm thick layer of fatty, etc. tissue. In this state, detection of the sentinel lymph node is performed. White light L1 is emitted from fluorescent lamp 100 at a regular frequency cycle of 50 Hz. Driven by stimulating light source-driver 112, stimulating light L2 having a wavelength of 790 nm is projected onto an area of tissue under examination 10 from semiconductor laser 111 at an emission cycle the reverse that of white light L1. Because stimulating light L2 is of a wavelength that is difficult for the tissue covering sentinel lymph node 11 to absorb, it passes through said tissue, and is absorbed by the indocyanine green accumulated on sentinel lymph node 11. Fluorescent light L4 is emitted from the indocyanine green accumulated on sentinel lymph node 11. The distribution of the wavelength spectrum of said fluorescent light L4 is shown in FIG. 4.

The reflected light L3 of white light L1 and the reflected light of stimulating light L2, and near-infrared fluorescent light L4 enter objective lens 121 and objective lens 125. Because light having a wavelength of 700 nm or smaller is cutoff by near-infrared fluorescent light cutoff filter 122, the reflected light of stimulating light L2 and near-infrared fluorescent light L4 are cutoff. Only light having a wavelength of 700 nm or larger from among the reflected light L3 of the white light L1 passes through near-infrared fluorescent light cutoff filter 122. After passing through near-infrared fluorescent light cutoff filter 122, said light reaches the examiner's eye through eyepiece 124. Because of this the examiner can see the normal image composed of the reflected light L3 passing through half mirror 123.

In addition, because light having a wavelength of 820 nm or smaller is cutoff by near-infrared fluorescent light cutoff filter 126, from among the light entering objective lens 125, the reflected light L3 of white light L1 and the reflected light of the stimulating light are cutoff. Only light having a wavelength of 820 nm from among near-infrared fluorescent light L4 passes through near-infrared fluorescent light cutoff filter 126. A portion of the near-infrared fluorescent light L4 is cutoff by near-infrared fluorescent light cutoff filter 126, however, because there are many fluorescent spectra in the wavelength band of 820 nm and above, no difficulties are encountered.

Near-infrared fluorescent light L4 is focused on the input face of image intensifier 127, which is an image magnifying tube, by objective lens 125. The electron flow is converted at image intensifier 127, and the portion of the magnified signal having a large light strength is converted to the white portion of a glossy black and white visible image. The visible image is reflected by mirror 130 and half mirror 123, and reaches the eye of the examiner. Because of this, the examiner can see the visible image reflected by half mirror 123.

The distance from the examiner's eye 12 to the area of tissue under examination 12, that is, the length of the optical path from the position of the eyepiece to the normal image and the distance from the examiners eye to fluorescent light panel 128, that is, although there is a difference in the length of the optical path from the eye of the observer to the visible image, because the normal image is superposed on the visible image by objective lens 121, eyepiece 124, objective lens 125 and lens 129, the examiner can observe the superposed image of the normal image and the visible image without hindrance.

According to the operation described above, because the wavelength band of stimulating light L2 is in the near-infrared wavelength range, even if the sentinel lymph node 11 is covered with fatty, etc. tissue, the stimulating light easily reaches the sentinel lymph node 11. In addition, because the indocyanine green accumulated in advance on the sentinel lymph node emits near-infrared fluorescent light upon irradiation thereof by stimulating light, the fluorescent light easily reaches the surface of the tissue. Because the near-infrared fluorescent image emitted by the area of tissue under examination is converted to a visible image by fluorescent light panel 128 and displayed, the sentinel lymph node can be easily detected with a high degree of accuracy.

In addition, white light L1, which is visible light, is irradiated onto the area of tissue under examination, and the normal image composed of the reflected light L3 is superposed on the position at which the visible image is focused, and focused. By observation of this focused image, the examiner can observe both the visible image and the normal image at the same time, and the position of the sentinel lymph node contained within the area of tissue under examination can be easily confirmed.

Because the sentinel lymph node detection system of the first embodiment described above is constructed in the form of a pair of goggles, when performing detection of the sentinel lymph node, the examiner can freely use both hands, and ease of operability of the system is thereby improved.

In addition, as an example of a different form, if the observation unit is constructed in the form of a microscope, when performing detection of the sentinel lymph node, the detailed position of thereof can be confirmed, whereby the fear that damage will be inflicted on the tissue in the surrounding vicinity, as well as the burden to the patient can be reduced.

Note that according to the current embodiment, an observation unit comprising a mirror 130, a half mirror 123, an objective lens 121, a lens 129 and an objective lens 124 has been employed, however, it is not limited to this; for example, it can be constructed so that observation is performed without use of a lens optical system. Observation means consisting of a variety of optical means combined in various configurations can be employed: For example, a configuration comprising a normal image optical path and an optical system for focusing a false image of a visible image; or conversely, a configuration for observing a visible image without employing a lens optical system, comprising a visible image optical path and an optical system for focusing a normal image; etc.

Figure 5:
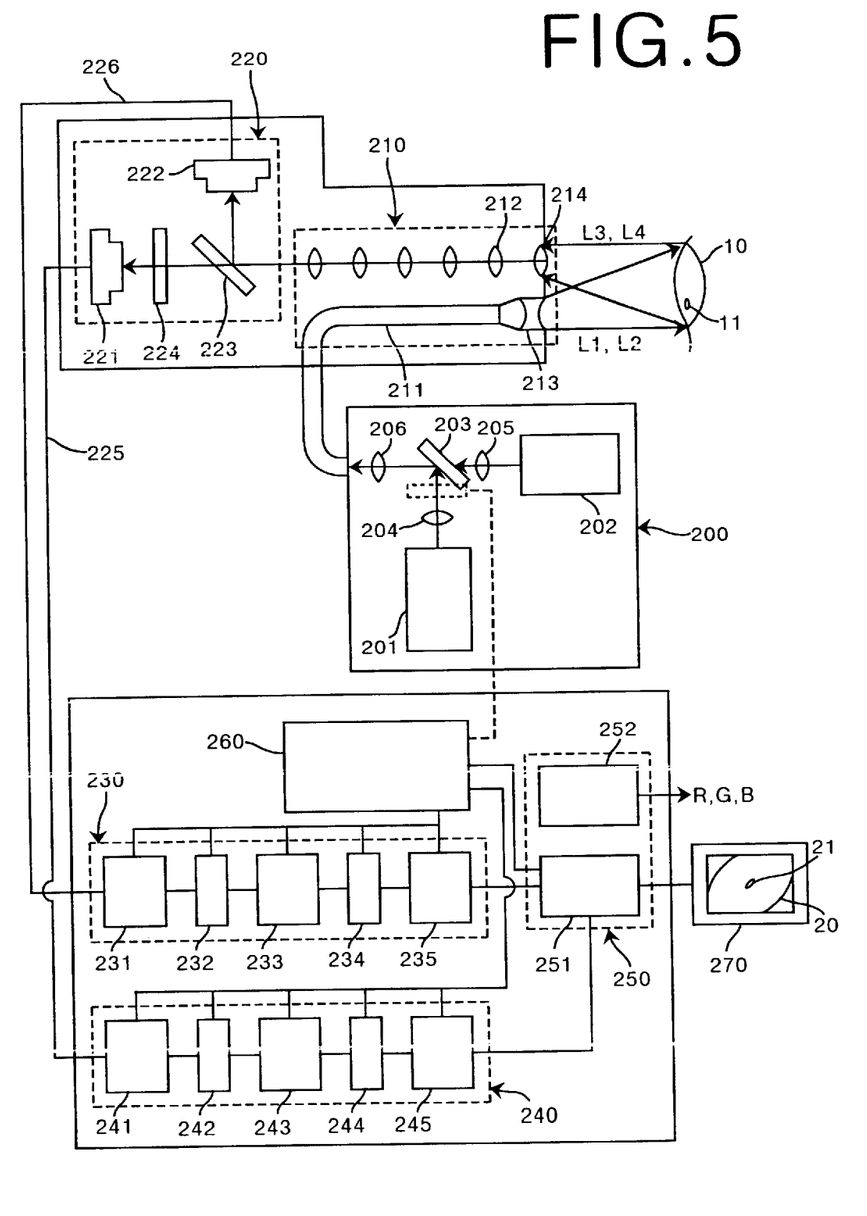
FIG. 5 is a schematic drawing of a first embodiment of a laparoscope implementing the present invention.

Next, a second preferred embodiment of the sentinel lymph node detection system according to the present invention implemented in a laparoscope will be explained. FIG. 5 is a schematic drawing of the configuration of a laparoscope implementing the second embodiment of the sentinel lymph node detection system according to the present invention. As in the first embodiment, the apparatus of the current embodiment facilitates detection of a sentinel lymph node by detecting the fluorescent light emitted from the sentinel lymph node upon irradiation of the near-infrared fluorescent colorant indocyanine green accumulated thereon, which has been injected into the patient in the vicinity of diseased tissue, by stimulating light projected onto the area of tissue under examination.

This laparoscope apparatus comprises an illumination unit 200 provided with a light source for producing normal-image photographing-use white light and fluorescent image photographing-use stimulating light, a laparoscope insertion portion 210, which is inserted into the body of the patient, a photographing unit 220 for photographing the normal image, which is composed of reflected light of the white light, and fluorescent images composed of the near-infrared fluorescent light emitted from the area of tissue under examination upon irradiation thereof by stimulating light, a normal-image forming unit 230 for performing the image processing to display the normal image as a color image, a fluorescent image forming unit 240 for performing the image processing to display the near-infrared fluorescent image as a stepped image corresponding to the degree of strength of the light, a superposed image forming means 250 for superposing the color image of the normal image and the stepped image of the fluorescent image, a control unit 260, which is connected to each unit, for controlling the operation timing, and a monitor 270 for displaying the normal image (the color image of the normal image) superposed by superposed image forming unit 250 and the fluorescent image.

Illuminating unit 200 comprises a semiconductor laser 201 for emitting fluorescent image-use stimulating light L2 having a wavelength of 790 nm, a white light source 202 for emitting normal image photographing-use white light L2, and a switching mirror 20 for switching the emission of the white light L2 and the emission of stimulating light L1 according to a predetermined timing.

Laparoscope insertion portion 210 is provided with a light guide 211 extending internally to the forward end thereof, and a 5-lens relay lens 212. An illuminating lens 213 and an objective lens 214 are provided in the forward end of light guide 211 and relay lens 212, that is, the forward end of laparoscope 210. Relay lens 211 is formed of composite glass fiber and is connected to illuminating unit 200.

Photographing unit 220 comprises a near-infrared use CCD 221 for photographing the fluorescent image formed of the near-infrared fluorescent light L4 entering via the relay lens 212, a color CCD 222 for photographing the normal image formed of the reflected light L3 of white light L1, a dichroic mirror 223 for separating the near-infrared fluorescent light L4 an the reflected light L3, a stimulating light cutoff filter 224 for removing the reflected light of the stimulating light L2 from the superposed near-infrared fluorescent light L4 and reflected light L3 of stimulating light L2, a CCD cable 225, which is connected to near-infrared use CCD 221, for transferring a photographed signal, and a CCD cable 226, which is connected to color CCD 222, for transferring a photographed signal. The dichroic mirror 223 passes light having a wavelength of 810 nm or larger, reflects in a perpendicular direction light having a wavelength of 810 nm or smaller, and cuts off light having a wavelength of 800 nm or smaller.

Normal-image forming means 230 comprises a signal processing circuit 231 for making a color image signal from the normal image photographed by CCD 222, an A/D converting circuit 232 for digitizing the color image signal obtained by said signal processing circuit 230, a normal image memory 233 for saving the digitized color image signal, a D/A conversion circuit 234 for performing DA conversion on the color image signal output from said normal image memory 233, and a normal image encoder 235 for converting the color image signal to a video signal.

Fluorescent image forming means 240 comprises a signal processing circuit 241 for performing sampling, clamping, blanking, amplification, etc. on the signal obtained by CCD 221 and making a green, stepped image signal, an A/D converting circuit 242 for digitizing the stepped image signal obtained by said signal processing circuit 241, a fluorescent image memory 243 for saving the digitized color image signal, a D/A conversion circuit 244 for performing DA conversion on the stepped image signal output from said fluorescent image memory 243, and a fluorescent image encoder 245 for converting the color image signal to a video signal.

Superposed image forming means 250 comprises a superimposer 251 for superposing the color image signal output from normal image encoder 235 on the stepped image signal output from fluorescent image encoder 245, and an RGB encoder 252 for converting the display signal, which is a video signal, to an RGB-type display signal.

Hereinafter, the operation of the laparoscope described above will be explained.

The same way as in the first embodiment, an example in which the procedures for detecting the sentinel lymph node with respect to a tumor located in the gastrointestinal tract of a patient will be use for the purpose of explanation.

First, at a predetermined time prior to the performance of an abdominal operation, an endoscope is inserted into the patient's gastrointestinal tract, and indocyanine green is locally injected into the vicinity of the tumor via an opening in a forceps. After the passing of a predetermined period of time, sentinel lymph node detection is performed using the laparoscope.

According to this laparoscope apparatus, photographing of the normal image and photographing of the near-infrared fluorescent image are performed in a time division manner. Exposure to the emission of white light L1 and reflected light L3 from color CCD 222 is performed for a little less than 30 ms every 60 ms. On the other hand, exposure to the emission of stimulating light L2 and near-infrared fluorescent light L4 from near-infrared use CCD 221 is performed in the opposite cycle, for a little less than 30 ms every 60 ms.

For the sake of simplicity in the explanation, first, the operations for displaying a normal image will be explained, and afterwards, the operation for displaying a fluorescent image will be explained. When a normal image is photographed, the switching mirror 203 within the illuminating unit 200 is driven by a signal from the controller 260 and moved to the position of the broken line so as to not interfere with the progress of white light L1, The white light L1 emitted from white light source 202 enters the light guide 211 by way of lens 205 and lens 206, and after being guided to the forward end of the laparoscope insertion portion 210, is projected by illuminating lens 213 onto the area of tissue under examination containing the sentinel lymph node 11.

The reflected light L3 of the white light L1 is focused by objective lens 214, guided via relay lens 212, reflected by dichroic mirror 223 and enters color CCD 222. The photographed signal of a normal image photoelectrically converted by color CCD 222 is output to signal processing circuit 231 via CCD cable 225.

The signal photographed by color CCD 222 is subjected to correlative double sampling, clamping, blanking, and amplifying, etc. by signal processing circuit 231, and afterwards, the luminescence and color signals are separated, and a color image signal obtained.

The color image signal obtained for each pixel by the signal processing circuit 231 is input to A/D converting circuit 232, and after digitization of each signal, is saved in normal image memory 233.

The color mage signal saved in the normal image memory 233 is matched to the display timing and DA converted by D/A converting circuit 234. The signal output from D/A converting circuit 234 is converted to a predetermined video signal by normal image encoder 235, input to superimposer 251 and output to monitor 270 and RGB decoder 252 as a video signal that has been superposed with a stepped fluorescent image, which is described below. The detailed operations of monitor 270 and RGB decoder 252 will be described below.

Next, the operation for cases in which a fluorescent image is to be displayed will be explained. Based on a signal from controller 260, the switching mirror 203 within the illuminating unit 200 is moved to the position of the solid line so that the stimulating light L2 emitted from the semiconductor laser 201 is reflected toward the light guide 211. The stimulating light L2 emitted from the semiconductor laser 201 advances toward switching mirror 203 via lens 204. The stimulating light L2 reflected by switching mirror 203 is directed into light guide 211 by lens 206, and after being guided to the forward end of the laparoscope insertion portion 210, is projected by illuminating lens 213 onto the area of tissue under examination containing the sentinel lymph node 11.

The near-infrared fluorescent light L4 emitted from the area of tissue under examination and the reflected light of the stimulating light L2 are focused by focusing lens 214, are guided by relay lens 212, pass through dichroic mirror 223 and enter stimulating light cutoff filter 224. The reflected light of stimulating light L2 is cutoff by the stimulating light cutoff filter, and the near-infrared light L4 enters near-infrared use CCD 221. The signal charge photoelectrically converted, corresponding to the light strength, by the photosensitive portion of near-infrared use CCD 221 is output to the signal processing circuit 241 of the fluorescent image forming means 240 by way of CCD cable 26.

The signal output from near-infrared use CCD 221 is subjected to correlative double sampling, clamping, blanking, and amplifying, etc. by signal processing circuit 241, and afterwards, a green stepped image signal, corresponding to the strength of the near-infrared fluorescent light, is made, and output to the A/D converting circuit 242.

Figure 6A:
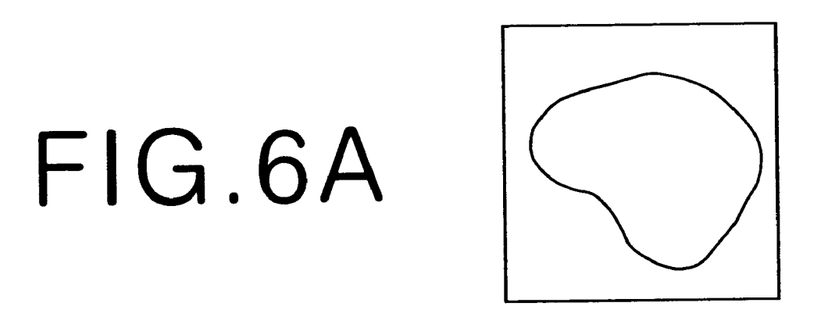
FIGS. 6A, 6B and 6C are provided for illustration and explanation of display images.
Figure 6B:
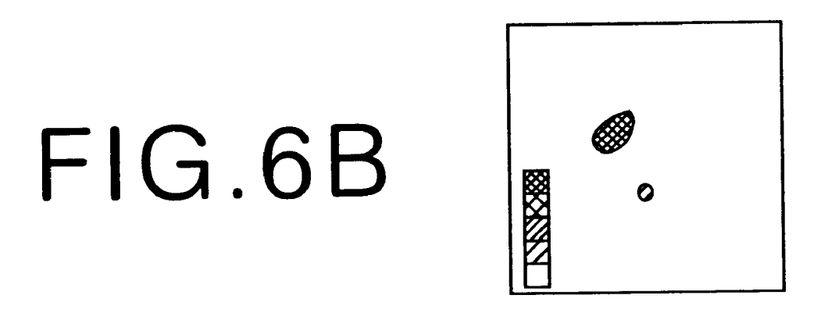
Figure 6C:
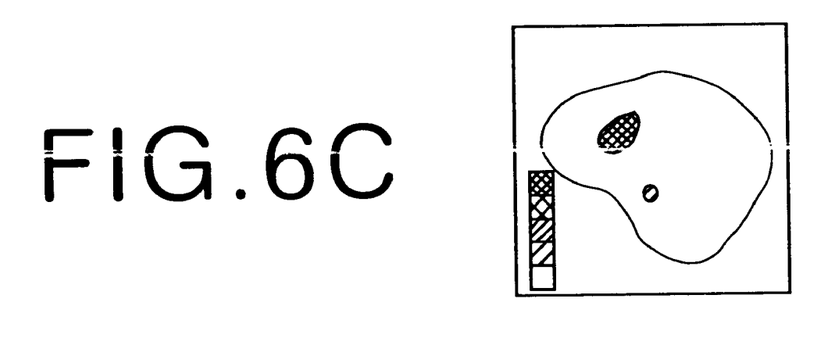

The color image signal obtained for each pixel by the signal processing circuit 231 is input to A/D converting circuit, and after digitization of each signal, is saved in normal image memory 233. The signal input to A/D converting circuit 242 is digitized and saved in fluorescent image memory 243. The digitized signal saved in the fluorescent image memory 243 is matched to the display timing and DA converted by D/A converting circuit 244. The signal output from D/A converting circuit 244 is converted to a predetermined video signal by fluorescent image encoder 235, input to superimposer 251. For example, if the normal image output from the normal image decoder 235 is a color image such as that shown in FIG. 6A, and the fluorescent image output from the fluorescent image decoder 245 is a stepped image such as that shown in FIG. 6B, the display image of the superposed color and stepped images is a display image such as that shown in FIG. 6C. This display image signal is output to monitor 270 and RGB decoder 252.

Monitor 270 converts the display signal, which is a video signal, and displays the display image. The red color of the tissue is the underlying tone of a normal image. Because the green color of a stepped image becomes denser corresponding to the light strength, the portion of the image having a large light strength, that is, the portion where the sentinel lymph node is, is displayed in yellow. The RGB decoder 252 reverse calculates each color signal (R, B, G) from the display image signal, and outputs the obtained signal to a direct color input apparatus (not shown), such as a printer, an image processing apparatus, etc. Note that the controller 260 controls the continuous series of operations described above.

According to the operations described above, the near-infrared fluorescent light emitted from the area of tissue under examination, into which indocyanine green has been locally injected in advance, is photographed by a fluorescent image photographing means, and by displaying the fluorescent image, which is a visible image, as a fluorescent image, even if the sentinel lymph node 11 is covered with fatty, etc. tissue, because it is easy to display a sentinel lymph node image 21, which is formed by the fluorescent light emitted from the sentinel lymph node in the fluorescent image, an examiner can quickly and easily detect the sentinel lymph node. In addition, because the fluorescent light emitted from the sentinel lymph node has been made into an image, it becomes possible to record or halt the display image as a still image, and the ease with which the sentinel lymph node can be detected is raised by a level.

In addition, by displaying the superposed display image of the superposed color image, which is formed by the reflected light L3 of the white light L1, and the green stepped image, which is formed corresponding to the light strength of the near-infrared fluorescent light, an examiner can observe the normal image and the fluorescent image at the same time, and because the zone where the sentinel lymph node is located is displayed in yellow, the position of the sentinel lymph node contained within the area of tissue under examination can easily be confirmed.

Note that because the normal image described above is displayed as a color image, the corresponding relationship of the actual area of tissue under examination 10 and the displayed area of tissue under examination 20 can be easily discerned; therefore, the actual position of sentinel lymph node 11 can easily be detected from the displayed position thereof.

Figure 7A:
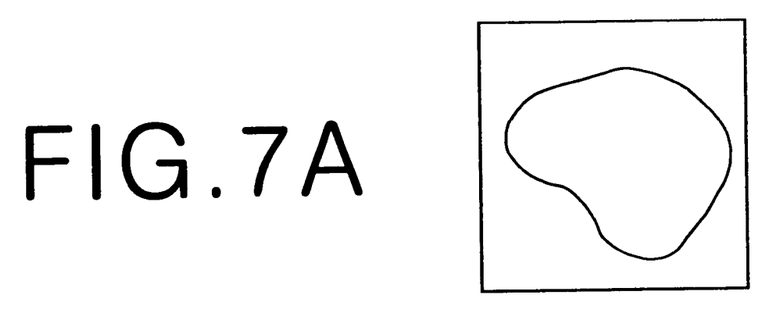
FIGS. 7A, 7B and 7C are provided for illustration and explanation of display images.
Figure 7B:
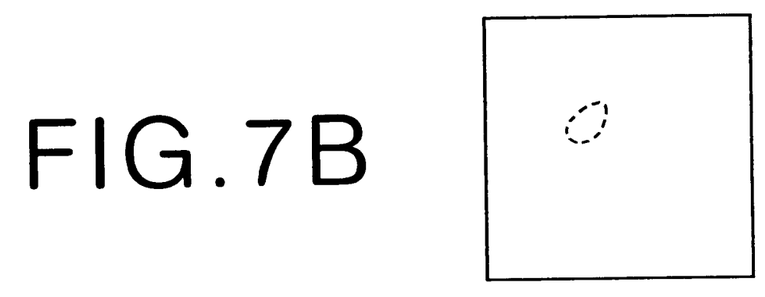
Figure 7C:
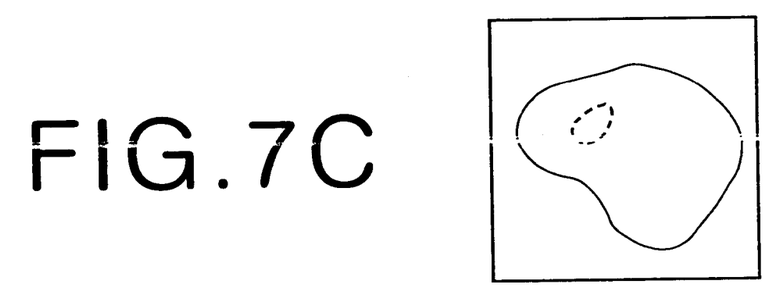

In addition, according to the current embodiment, although a near-infrared fluorescent image is displayed utilizing a stepped green image, as an alternative example, as shown in FIG. 7B, photographed zones having near-infrared fluorescent light strength per unit of area above a predetermined value are shown as closed zones, said image is superposed with the normal image shown in FIG. 7A, and an image such as that shown in FIG. 7C can be displayed. In this case, because it is easy to discern the zone where the sentinel lymph node is, the ease with which the sentinel lymph node can be detected is raised by a level.

Figure 8A:
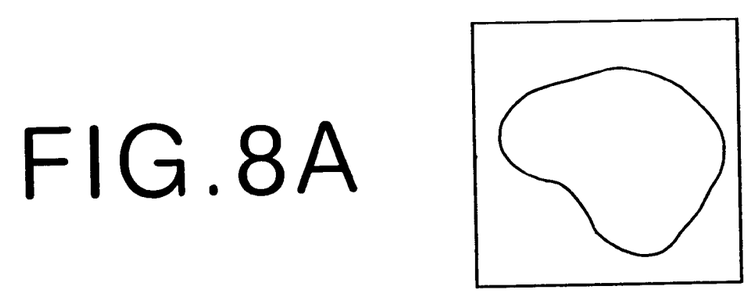
FIGS. 8A, 8B and 8C are provided for illustration and explanation of display images.
Figure 8B:
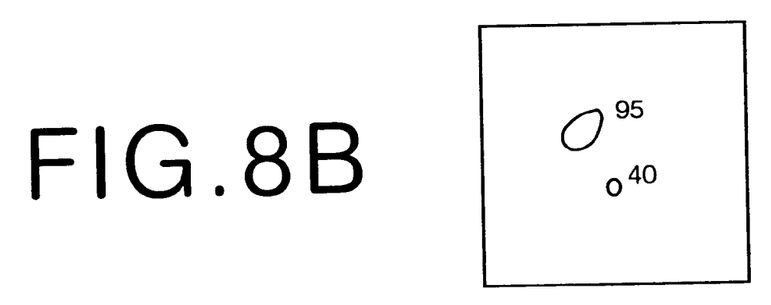
Figure 8C:
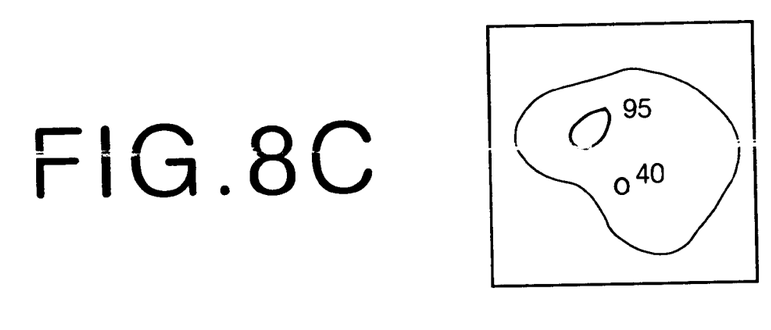

Further, as another example, as shown in FIG. 8B, the light strength of photographed zones having near-infrared fluorescent light strength per unit of area above a predetermined value are shown as numbers, said image is superposed with the normal image shown in FIG. 8A, and an image such as that shown in FIG. 8C can be displayed. In this case, even for cases in which the indocyanine green has reached several lymph nodes, by referring to the displayed numbers, the sentinel lymph node can be confirmed.

Still further, by constructing the sentinel lymph node detection system described above in the form of a laparoscope, when sentinel lymph node detection is to be performed, there is no need to perform an abdominal operation, and the burden on the patient is reduced.

On the other hand, for cases in which a sentinel lymph node detection system employing the photographing apparatus described above is used during the performance of an abdominal operation, it is possible to simply construct the photographing apparatus in the form of a television camera; it can also be constructed in the form of a pair of goggles.

Note that according to the first and second embodiments, because indocyanine green, which is a cyanine colorant having a largest absorbable wavelength in the near-infrared wavelength band, is employed, not only is it not easily affected by absorption by tissue or random dispersion, because background autofluorescence also produces no adverse effect, when the fluorescent light is focused or photographed, only the fluorescent light that is the objective can easily be focused or photographed, and the reliability of the sentinel lymph node detection system is thereby improved.

What is claimed is:

1. A sentinel lymph node detection method, comprising:

focusing a fluorescent image composed of fluorescent light having a wavelength band within the near-infrared wavelength band emitted from a near-infrared fluorescent colorant, which emits fluorescent light having a wavelength band within the near-infrared wavelength band, that has been injected into the area of tissue under examination in the vicinity of a diseased portion, which includes the sentinel lymph node, upon irradiation thereof by stimulating light; and converting said focused fluorescent image composed of fluorescent light having a wavelength band within the near-infrared wavelength band to a visible image, wherein a normal image composed of the reflected light reflected by the area of tissue under examination that has been irradiated by an illuminating light composed of visible light and said visible image are superposed and observed.

2. A sentinel lymph node detection method as defined in claim 1, wherein said normal image is superposed on said visible image and focused, and said focused image and said visible image are viewed.

3. A sentinel lymph node detection method, comprising:

photographing a fluorescent image composed of fluorescent light having a wavelength band within the near-infrared wavelength band is emitted from a near-infrared fluorescent colorant, which emits fluorescent light having a wavelength band within the near-infrared wavelength band, that has been injected into the area of tissue under examination in the vicinity of the diseased portion, which includes the sentinel lymph node, upon irradiation thereof by stimulating light;

forming a visible image based on said photographed fluorescent image composed of fluorescent light having a wavelength band within the near-infrared wavelength band;

displaying said visible image;

photographing a normal image composed of the reflected light reflected by the area of tissue under examination that has been irradiated by an illuminating light;

superposing said normal image with said visible image; and displaying the superposed image.

4. A sentinel lymph node detection method as defined in claim 3, wherein said normal image is photographed as a color image.

5. A sentinel lymph node detection system comprising:

a stimulating light projecting means for projecting stimulating light, which has a wavelength in the wavelength range of light that stimulates the near-infrared fluorescent colorant, onto the area of tissue under examination in the vicinity of the diseased portion, which includes the sentinel lymph node and into which said near-infrared fluorescent colorant for emitting fluorescent light having a wavelength band within the near-infrared wavelength band has been injected in advance;

a fluorescent light image focusing means for focusing the fluorescent light having a wavelength band within the near-infrared wavelength band emitted from the near-infrared fluorescent colorant injected into the area of tissue under examination;

a visible-image converting means for converting the fluorescent image having a wavelength band within the near-infrared wavelength band focused by the fluorescent light image focusing means to a visible image composed of light having a wavelength band within the visible spectrum;

an illuminating light projecting means for projecting illuminating light composed of visible light onto the area of tissue under examination; and an observation means for superposing a normal image, which is composed of the reflected light reflected by the area of tissue under examination upon illumination thereof by said illuminating light, with aforementioned visible image, and observing said normal image superposed with said visible image.

6. A sentinel lymph node detection system as defined in claim 5, further comprising:

an image focusing means for focusing the normal image and the visible image superposed by the observation means; and an observation optical means for observing the image focused by said image focusing means and the visible image.

7. A sentinel lymph node detection system comprising:

a stimulating light projecting means for projecting stimulating light, which has a wavelength in the wavelength range of light that stimulates the near-infrared fluorescent colorant, onto the area of tissue under examination in the vicinity of the diseased portion, which includes the sentinel lymph node and into which said near-infrared fluorescent colorant for emitting fluorescent light having a wavelength band within the near-infrared wavelength band has been injected in advance;

a fluorescent image photographing means for photographing the fluorescent light having a wavelength band within the near-infrared wavelength band emitted from the near-infrared fluorescent colorant injected into the area of tissue under examination;

a fluorescent image forming means for forming a visible image based on the fluorescent image having a wavelength band within the near-infrared wavelength band photographed by said fluorescent image photographing means; and a display means for displaying said visible image;

an illuminating light projecting means for projecting illuminating light composed of visible light onto the area of tissue under examination;

a normal image photographing means for photographing the normal image composed of the reflected light reflected by the area of tissue under examination upon illumination thereof by the illuminating light;

a normal-image forming means for forming a normal image from the photographed signal photographed by the normal image photographing means; and a superposed image forming means for forming a superposed image of said normal image superposed with said visible image, wherein the display means displays the superposed image.

8. A sentinel lymph node detection system as defined in claim 7, wherein said normal image photographing means is a color photographing means for photographing a color image.

9. A sentinel lymph node detection system as defined in claim 5, 6, 7 or 8, wherein said fluorescent light image focusing means, said converting means and said observation means, or said fluorescent image forming means, said normal image photographing means, said normal-image forming means, said superposed image forming means and said display means are constructed in the form of a pair of goggles.

10. A sentinel lymph node detection system as defined in claim 5, 6, 7 or 8, wherein said fluorescent light image focusing means, said converting means and said observation means, or said fluorescent image forming means, said normal image photographing means, said normal-image forming means, said superposed image forming means and said display means are constructed in the form of a laparoscope system.

11. A sentinel lymph node detection system as defined in claim 5, 6, 7 or 8, wherein said fluorescent light image focusing means, said converting means and said observation means, or said fluorescent image forming means, said normal image photographing means, said normal-image forming means, said superposed image forming means and said display means are constructed in the form of a microscope system.

12. A sentinel lymph node detection system as defined in claim 1, 3, 3, 4, 5, 6, 7 or 8, wherein the wavelength band of the stimulating light is 700 nm or longer.

13. A sentinel lymph node detection system as defined in claim 9, wherein the wavelength band of the stimulating light is 700 nm or longer.

14. A sentinel lymph node detection system as defined in claim 10, wherein the wavelength band of the stimulating light is 700 nm or longer.

15. A sentinel lymph node detection system as defined in claim 11, wherein the wavelength band of the stimulating light is 700 nm or longer.

16. A sentinel lymph node detection system as defined in claim 1, 2, 3, 4, 5, 6, 7 or 8, wherein when the near-infrared fluorescent colorant is irradiated with light, the largest absorption wavelength of said near-infrared colorant is 700 nm or longer.

17. A sentinel lymph node detection system as defined in claim 9, wherein when the near-infrared fluorescent colorant is irradiated with light, the largest absorption wavelength of said near-infrared colorant is 700 nm or longer.

18. A sentinel lymph node detection system as defined in claim 10, wherein when the near-infrared fluorescent colorant is irradiated with light, the largest absorption wavelength of said near-infrared colorant is 700 nm or longer.

19. A sentinel lymph node detection system as defined in claim 11, wherein when the near-infrared fluorescent colorant is irradiated with light, the largest absorption wavelength of said near-infrared colorant is 700 nm or longer.

20. A sentinel lymph node detection system as defined in claim 13, wherein when the near-infrared fluorescent colorant is irradiated with light, the largest absorption wavelength of said near-infrared colorant is 700 nm or longer.

21. A sentinel lymph node detection system as defined in claim 1, 2, 3, 4, 5, 6, 7 or 8, wherein said near-infrared fluorescent colorant is a cyanine colorant.

22. A sentinel lymph node detection system as defined in claim 9, wherein said near-infrared fluorescent colorant is a cyanine colorant.

23. A sentinel lymph node detection system as defined in claim 10, wherein said near-infrared fluorescent colorant is a cyanine colorant.

24. A sentinel lymph node detection system as defined in claim 11, wherein said near-infrared fluorescent colorant is a cyanine colorant.

25. A sentinel lymph node detection system as defined in claim 13, wherein said near-infrared fluorescent colorant is a cyanine colorant.

26. A sentinel lymph node detection system as defined in claim 13, wherein said near-infrared fluorescent colorant is a cyanine colorant.

27. A sentinel lymph node detection system as defined in claim 1, 2, 3, 4, 5, 6, 7 or 8, wherein said near-infrared fluorescent colorant is a indocyanine green.

28. A sentinel lymph node detection system as defined in claim 9, wherein said near-infrared fluorescent colorant is a indocyanine green.

29. A sentinel lymph node detection system as defined in claim 10, wherein said near-infrared fluorescent colorant is a indocyanine green.

30. A sentinel lymph node detection system as defined in claim 11, wherein said near-infrared fluorescent colorant is a indocyanine green.

31. A sentinel lymph node detection system as defined in claim 13, wherein said near-infrared fluorescent colorant is a indocyanine green.

32. A sentinel lymph node detection system as defined in claim 13, wherein said near-infrared fluorescent colorant is a indocyanine green.

33. A sentinel lymph node detection system as defined in claim 14, wherein said near-infrared fluorescent colorant is a indocyanine green.

34. A sentinel lymph node detection system comprising:
   a stimulating light projecting unit for projecting stimulating light, which has a wavelength in the wavelength range of light that stimulates the near-infrared fluorescent colorant, onto the area of tissue under examination in the vicinity of the diseased portion, which includes the sentinel lymph node and into which said near-infrared fluorescent colorant for emitting fluorescent light having a wavelength band within the near-infrared wavelength band has been injected in advance;
   a fluorescent light image focusing unit for focusing the fluorescent light having a wavelength band within the near-infrared wavelength band emitted from the near-infrared fluorescent colorant injected into the area of tissue under examination;
   a visible-image converting unit for converting the fluorescent image having a wavelength band within the near-infrared wavelength band focused by the fluorescent light image focusing unit to a visible image composed of light having a wavelength band within the visible spectrum;
   an illuminating light projecting unit for projecting illuminating light composed of visible light onto the area of tissue under examination; and
   an observation unit for superposing a normal image, which is composed of the reflected light reflected by the area of tissue under examination upon illumination thereof by said illuminating light, with aforementioned visible image, and observing said normal image superposed with said visible image.

35. A sentinel lymph node detection system comprising:
   a stimulating light projecting unit for projecting stimulating light, which has a wavelength in the wavelength range of light that stimulates the near-infrared fluorescent colorant, onto the area of tissue under examination in the vicinity of the diseased portion, which includes the sentinel lymph node and into which said near-infrared fluorescent colorant for emitting fluorescent light having a wavelength band within the near-infrared wavelength band has been injected in advance;

a fluorescent image photographing unit for photographing the fluorescent light having a wavelength band within the near-infrared wavelength band emitted from the near-infrared fluorescent colorant injected into the area of tissue under examination;

a fluorescent image forming unit for forming a visible image based on the fluorescent image having a wavelength band within the near-infrared wavelength band photographed by said fluorescent image photographing unit;

a display unit for displaying said visible image;

an illuminating light projecting unit for projecting illuminating light composed of visible light onto the area of tissue under examination;

a normal image photographing unit for photographing the normal image composed of the reflected light reflected by the area of tissue under examination upon illumination thereof by the illuminating light;

a normal-image forming unit for forming a normal image from the photographed signal photographed by the normal image photographing unit; and a superposed image forming unit for forming a superposed image of said normal image superposed with said visible image, wherein the display unit displays the superposed image.

* * * * *